(12) United States Patent
Arnisolle

(10) Patent No.: US 6,893,420 B2
(45) Date of Patent: May 17, 2005

(54) SYRINGE FOR AUTOMATIC INJECTION OF AN EXTEMPORANEOUS MIXTURE

(75) Inventor: Yves Arnisolle, Saint Genis Laval (FR)

(73) Assignee: SEDAT, Irigny (FR)

( * ) Notice: Subject to any disclaimer, the term of this patent is extended or adjusted under 35 U.S.C. 154(b) by 141 days.

(21) Appl. No.: 10/168,028

(22) PCT Filed: Oct. 18, 2001

(86) PCT No.: PCT/FR01/03232

§ 371 (c)(1),
(2), (4) Date: Jun. 18, 2002

(87) PCT Pub. No.: WO02/34316

PCT Pub. Date: May 2, 2002

(65) Prior Publication Data

US 2002/0183690 A1 Dec. 5, 2002

(30) Foreign Application Priority Data

Oct. 19, 2000 (FR) .............................. 00 13405

(51) Int. Cl.⁷ .................... A61M 5/00; A61M 37/00; A61M 5/32
(52) U.S. Cl. ................... 604/135; 604/138; 604/136; 604/191; 604/90; 604/194
(58) Field of Search ..................... 604/135–138, 604/190–194, 89, 90–99, 230, 220, 209, 201, 67, 155, 506, 187, 80–88; 600/432, 500, 384, 514

(56) References Cited

U.S. PATENT DOCUMENTS 4,723,937 A * 2/1988 Sarnoff et al. ............... 604/90
4,820,286 A * 4/1989 van der Wal ................. 604/89
4,822,340 A * 4/1989 Kamstra ....................... 604/135
5,281,198 A * 1/1994 Haber et al. .................. 604/86

FOREIGN PATENT DOCUMENTS

| EP | 0 405 320 A2 | 1/1991 |
| EP | 0 562 671 A1 | 9/1993 |
| WO | WO 94 09839 | 5/1994 |

* cited by examiner

Primary Examiner—Nicholas D. Lucchesi
Assistant Examiner—Roz Maiorino
(74) Attorney, Agent, or Firm—Sughrue Mion, PLLC

(57) ABSTRACT

The syringe (10) for self-injecting an extemporaneous mixture comprises:

a body (60) containing at least two substances (36, 38) initially separated by an intermediate piston (32), which body (60) has two relatively movable portions (64, 66) that are movable between an initial position in which the two substances (36, 38) are separate and a final position in which the two substances (36, 38) are mixed together to form an extemporaneous mixture;

automatic means (70, 72) for injecting the extemporaneous mixture out from the body (60) in order to proceed with injection; and latch means (73) for preventing triggering of the automatic injection means (70, 72).

The syringe includes locking means (154, 109) for locking the latch means (73) so as to prevent the automatic injection means (70, 72) being triggered until the two substances have finished being mixed together.

4 Claims, 7 Drawing Sheets

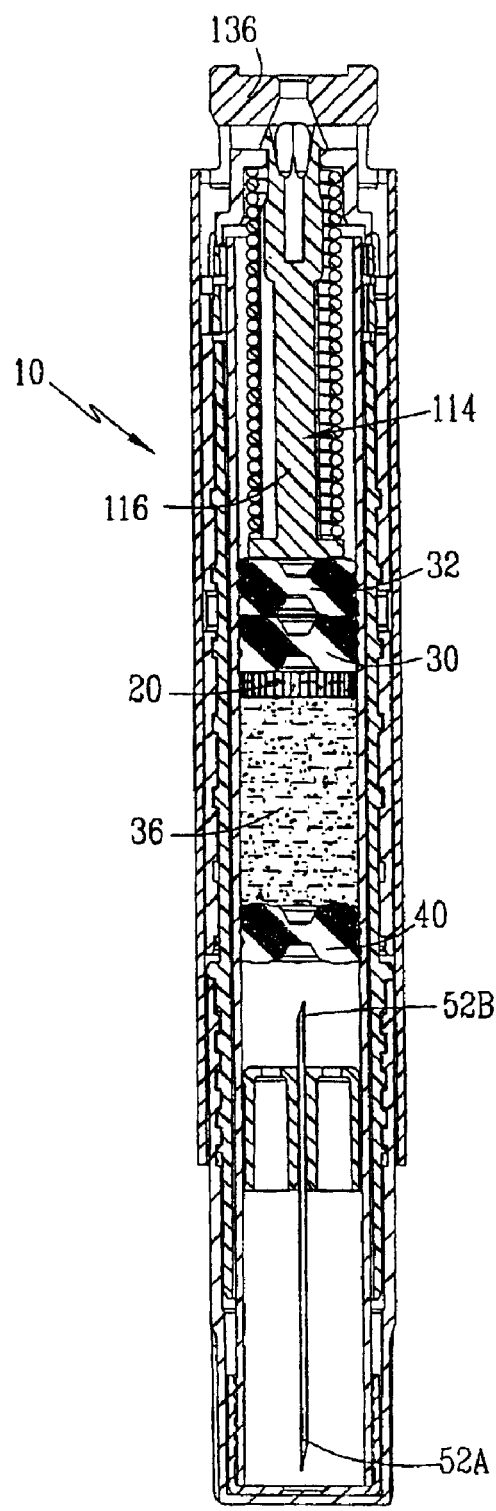 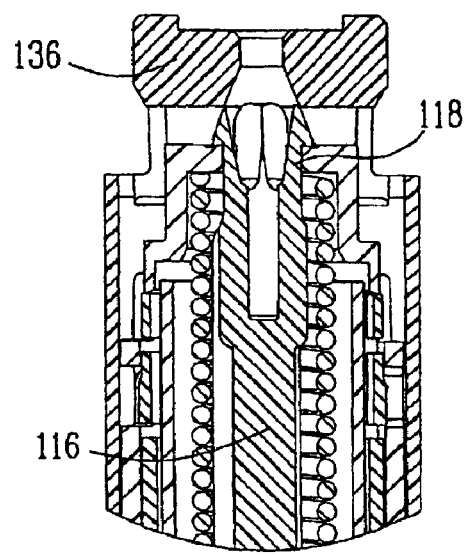
FIG.7A
FIG.7B

SYRINGE FOR AUTOMATIC INJECTION OF AN EXTEMPORANEOUS MIXTURE

BACKGROUND OF THE INVENTION

The present invention relates to a syringe for injecting an extemporaneous mixture, the syringe being of the type comprising:

- a body containing at least two substances initially separated by an intermediate piston, which body has two relatively movable portions that are movable between an initial position in which the two substances are separate and a final position in which the two substances are mixed together to form an extemporaneous mixture;
- automatic means for injecting the extemporaneous mixture out from the body in order to proceed with injection; and
- latch means for preventing triggering of the automatic injection means.

Such a syringe is described in particular in document EP-A-0 219 899 with reference to FIGS. 14 and 15.

In that document, the syringe includes an injection cartridge received in a syringe casing. The cartridge constitutes a tubular tank containing the substances to be injected. These substances are initially separated by moving pistons. The means for mixing the substances are formed by a lateral projection of the cartridge. This locally increases the internal section of the cartridge and defines a passage enabling the substances to go past the separator pistons.

Means for automatically actuating the rear wall in order to inject the extemporaneous mixture are also provided in the casing. They essentially comprise a spring-loaded pusher together with means for releasing the pusher. In order to avoid accidental release of the means for injecting the extemporaneous mixture, a removable member is provided for latching the automatic injection means. That latching member has a pin which is initially engaged between resilient tongues that retain the spring. The pin prevents the spring being released by preventing the tongues from deforming.

In order to reconstitute the extemporaneous mixture, at least a portion of the syringe casing can be moved relative to the cartridge so that when said portion of the casing is caused manually to slide over the cartridge, the pusher urges the moving rear partition of the cartridge so as to move it towards the front partition, thereby causing the substances for injection to be mixed together by passing through the lateral projection.

After the substances for injection have been mixed together, and after the latching member has been withdrawn, the spring of the actuator means is released, thereby causing the previously mixed-together substances to be injected automatically.

In practice, it is found that the operator sometimes releases the spring of the actuator means to proceed with injection before the substances have been fully mixed together, with the moving portion of the casing not having been caused to slide along its entire stroke along the cartridge. Extemporaneous mixing is then either not performed or is performed incompletely only, such that it has the wrong concentrations of the various ingredients initially contained in the cartridge.

The effect of this faulty operation is particularly unfortunate in that self-injection syringes are commonly used in emergency situations where people who are on their own need to inject themselves. Stress can then cause the user to act hastily without ensuring that the mixture has been properly and completely reconstituted.

SUMMARY OF THE INVENTION

An object of the invention is to propose a solution to this problem, so as to avoid that extemporaneous mixing is implemented incompletely for an injection.

To this end, the invention provides a syringe of the above-specified type, characterized in that it comprises locking means for locking the latch means that prevent the automatic injection means from being triggered before the two substances have finished being mixed together.

In particular embodiments of the invention, the syringe further comprises one or more of the following characteristics:

- the latch means comprise a latch member movable between an active position for latching the automatic injection means, and an inactive position where the automatic injection means are not latched, the locking means including complementary hooking profiles for hooking by elastic engagement provided on said latch member and on a first moving portion of the body, said complementary hooking profiles being normally mutually engaged, and the second moving portion of the body includes at least one surface for disengaging the complementary hooking profiles and adapted to disengage said complementary hooking profiles only when the two moving portions of the body are in their final position;
- said complementary hooking profiles comprise firstly at least one hook secured to said latch member, and secondly at least one slot formed in said first moving portion, the or each hook being urged elastically to be received at least in part in an associated slot, and the or each engagement surface is adapted to extend in the or each slot to push the or each associated hook fully out from the slot only once the two moving portions are in their final position; and
- said latch member (73) is removable.

BRIEF DESCRIPTION OF THE DRAWINGS

The invention will be better understood on reading the following description given purely by way of example and made with reference to the drawings, in which:

FIG. 7A is a longitudinal section view of the syringe, prior to injection, the latch member being withdrawn;

FIG. 7B is a longitudinal section view on a larger scale showing the rear end of the syringe in its FIG. 7A state.

DETAILED DESCRIPTION OF THE INVENTION

Figure 1:
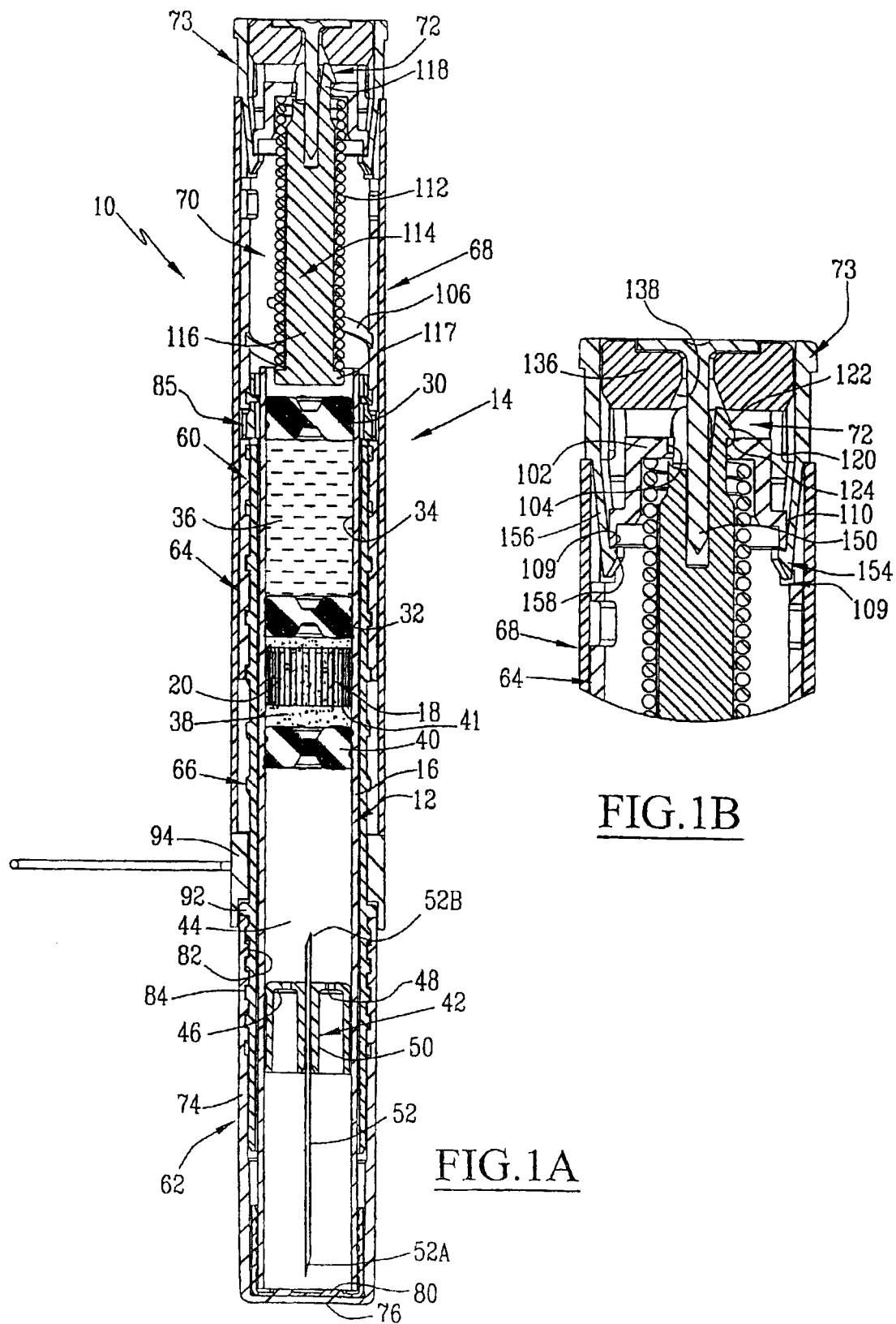
FIG. 1A is a longitudinal section view of a syringe of the invention prior to use.
FIG. 1B is a view on a larger scale in section showing the rear end of the FIG. 1A syringe.

The self-injection syringe 10 of the invention is shown in FIG. 1 in its initial state which corresponds to storage prior to use. It comprises an injection cartridge 12 and an outer casing 14 in which the cartridge is mounted.

The injection cartridge 12 comprises a substantially cylindrical tube 16. The inside surface of the tube is generally cylindrical and of circular section. In its intermediate portion, the tube has a middle segment 18 where its inside surface presents a profile defining at least one flow passage enabling the two initially separate substances contained in the tube to be mixed together extemporaneously.

The middle segment 18 lies between segments having smooth cylindrical inside surfaces without any projecting or indented profiles.

The segment 18 has fluting 20 extending parallel to generator lines of the tube. The fluting 20 projects from the cylindrical inside surface of the tube. It defines parallel channels forming passages to allow a fluid to flow.

From a rear end, the injection cartridge 12 comprises a moving partition 30 forming a piston whose cylindrical side surface is provided with peripheral ribs to provide liquid- and gas-tight sealing between itself and the inside surface of the tube 16.

An intermediate piston 32 is placed further forwards inside the tube but behind the segment 18. It co-operates with the partition 30 to define a housing 34 for a solvent 36. On its side surface, the intermediate piston 32 presents peripheral ribs for co-operating with the inside surface of the tube 16 to provide sealing against liquids and gases. This piston is of a length that is shorter than the length of the fluting 20.

In front of the intermediate piston 32, in the segment 18, there is located a mass of powder 38 containing a medically active substance. It is held against the intermediate piston 32 by a front moving partition 40 identical to the rear moving partition 30. The piston 32 and the partition 40 thus initially define a chamber 41 for confining the powder 38.

The mass of powder 38 could be replaced by a liquid.

A sliding needle carrier 42 forming a front wall of the cartridge is located beyond the partition 40 towards the front of the tube 16. It is shown in FIG. 1 in its position retracted inside the tube.

The needle carrier 42 and the front partition 40 define between them an empty space 44 filled with air. The needle carrier 42 is formed with a cup 46 of plastics material with its end wall facing towards the front partition 40 and with its side wall pressed slidably against the inside surface of the tube 16. The cup 46 has vents 48 enabling the air contained in the space 44 to escape to the outside. Integrally molded with the bottom wall of the cup there is an internal axial stud 50 for securing an injection needle 52.

The needle 52 passes right through the cup 46. It is initially fully received inside the tube 16. At its ends it has a front chamfered tip 52A and a rear chamfered tip 52B. The rear tip forms an end for puncturing the front partition 40.

The casing 14 essentially comprises a body 60 made up of a front cap 62 and a rear cap 64 joined together by an intermediate sleeve 66, a handle 68 that is movable relative to the body 60, automatic means 70 for actuating the moving rear partition of the cartridge for injection purposes, and means 72 for releasing the actuator means 70. The automatic actuator means 70 associated with the release means 72 are adapted to ensure that when they are triggered, an extemporaneous mixture previously prepared in the syringe is injected. The casing also has a latch member 73 for latching the automatic means 70 for actuating the rear partition.

The front cap 62 is permanently secured to the intermediate sleeve 66 by screw fastening and resilient engagement of complementary projecting and recessed profiles. Together with the cartridge tube 16 which bears against the front cap 62, these items form a tubular tank of the syringe relative to which the rear cap 64 is movable in order to move the rear partition 30 along a stroke for preparing the extemporaneous mixture.

The front cap 62 comprises a tubular segment 74 of inside diameter greater than the outside diameter of the tube 16 and a closing end wall 76 having in its center a weak region suitable for being pierced by the injection needle 52. The front end of the tube 16 bears axially against the closing wall 76. Between them there is a perforatable membrane 80 that serves initially to isolate the needle 52 from the outside environment.

On the inside surface of the tubular segment 74, the front cap presents an inside thread 82 which is connected to the intermediate sleeve 66 by screw engagement.

Figure 2:
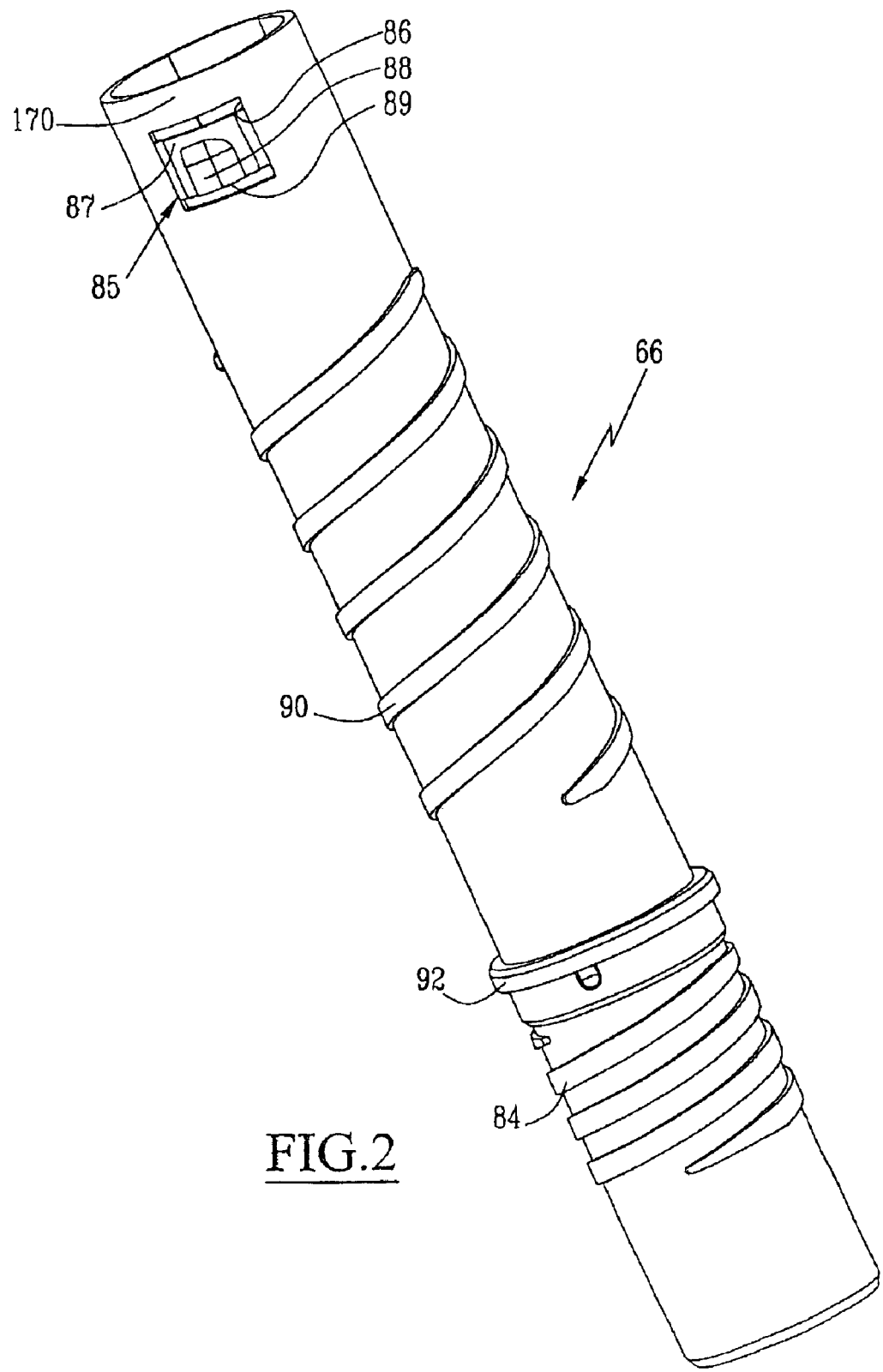
FIG. 2 is a perspective view of the intermediate sleeve of the syringe of the invention.

This intermediate sleeve which is shown on its own in FIG. 2 is generally tubular in shape. Its inside diameter is constant and corresponds substantially to the outside diameter of the cartridge 12.

At its front end towards the injection needle 52, the intermediate sleeve 66 presents an outside thread 84 suitable for co-operating with the thread 82 that is provided on the inside of the front cap 62.

In the vicinity of its rear end, the intermediate sleeve 66 has resilient members 85 for preventing the intermediate sleeve 66 moving relative to the rear cap 64. These resilient members 85 are integrally molded with the intermediate sleeve 66. They are placed in two diametrically opposite through slots 86 formed in the main portion of the intermediate sleeve 66 close to its rear end.

Each resilient member 85 comprises a resilient limb 87 connected to the sleeve along one of the edges of the slot 86, the connection extending along a generator line of the sleeve. In addition, each resilient member has a projection 88 formed on the outside surface of the resilient limb 87. This projection co-operates with the edge of each limb 87 that faces towards the front of the intermediate sleeve to define an abutment surface 89 suitable for co-operating with a complementary surface of the rear cap in order to hold them axially relative to each other in a predetermined position, the projection 88 being received in a complementary housing of the rear cap, as described below.

The limbs 87 are naturally urged outwards, with the projections 88 then projecting from the outer cylindrical surface of the intermediate sleeve 66.

In its main portion, between the slots 86 and the thread 84, the intermediate sleeve 66 presents a thread 90 having the same handedness as the thread 84.

The pitch of the thread 90 is large. Thus, for example, the helical thread 90 makes three turns over the length of the sleeve 66.

Between the two threads 84 and 90, the intermediate sleeve 66 has a peripheral abutment 92 for preventing a removable safety latch ring 94 (visible in FIG. 1A) from moving in translation.

Figure 3:
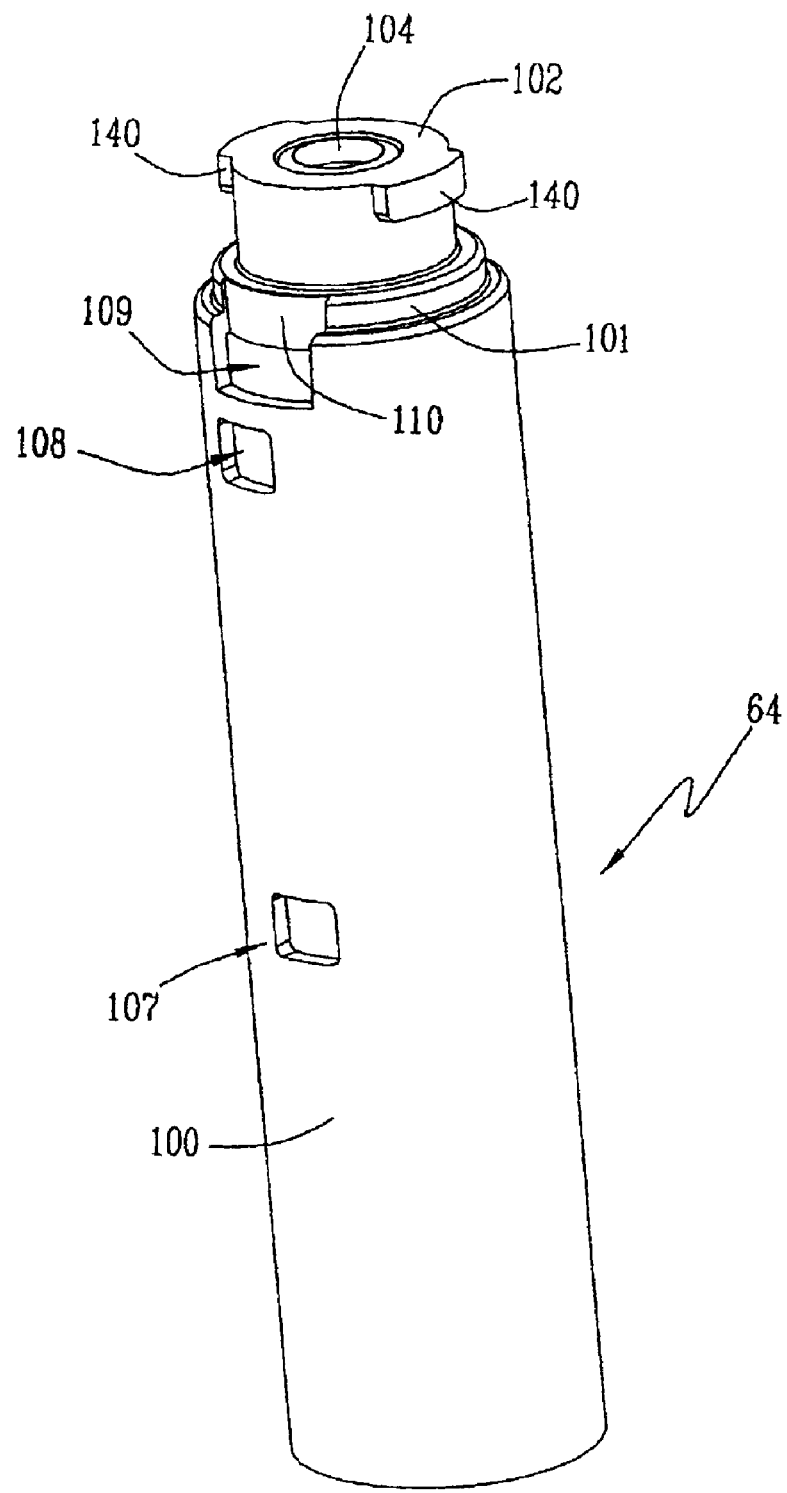
FIG. 3 is a perspective view of the rear cap of the syringe.

The rear cap 64 which is shown on its own in FIG. 3 is formed by a tubular segment 100 of constant circular inside section equal to the outside section of the intermediate sleeve 66. Towards its rear end, the tubular segment 100 is extended by a coaxial cylindrical segment 101 having inside and outside diameters that are smaller than those of the tubular segment 100. The rear end of the cylindrical segment 101 is closed in part by an end wall 102 that presents a central passage 104.

At its open end remote from the end wall 102, the rear cap 64 presents an inside thread 106 that can be seen in FIG. 1A and that is suitable for co-operating with the thread 90 formed on the outside surface of the intermediate sleeve 66. This thread is formed by a helical groove formed in the thickness of the cap. The pitch of this helical groove is equal to the pitch of the thread 90. It turns through 360° along the threaded length of the cap.

The middle portion of the tubular segment 100 of the rear cap 64 has a first pair of diametrically opposite housings 107 adapted, while the syringe is in its initial state, to receive the projections 88 provided at the ends of the limbs 87.

In addition, a second pair of diametrically opposite housings 108 is provided in the cylindrical inside surface of the cap 64 slightly in front of the cylindrical segment 101. These housings 108 are adapted, at the end of reconstituting the extemporaneous mixture, to receive the projections 88 and thus prevent the intermediate sleeve from moving axially.

In addition, the rear cap 64 has two diametrically opposite slots 109 in front of the end wall 102 for receiving the ends of hooks of means for locking the latch member 73. The member 73 is described below, in particular with reference to FIG. 5.

The slots 109 are formed through the tubular segment 100 at the base of the cylindrical segment 101.

In addition, extending the slots 109, the smaller diameter cylindrical segment 101 has outside flats 110 reducing the thickness of the wall defining the cylindrical segment 101.

The distance between these opposite flats 110 is less than the outside diameter of the intermediate sleeve 66.

As shown in FIG. 1, the cartridge 12 is received inside the casing 14 and it is held between the closing end walls 76 at the front and the actuator means 70 at the rear for actuating the rear piston of the cartridge.

These actuator means 70 essentially comprise an actuator spring 112 having a pusher 114 placed therein. The pusher comprises a rod 116 provided at its front end with a head 117 for pressing against the rear partition 30 of the cartridge.

The rod 116 is extended outwardly by two resilient tongues 118 extending substantially parallel. These tongues are shown on a larger scale in FIG. 1B. Each has an outwardly directed lip 120 at its end presenting in section a chamfered rear portion 122 and a front face 124 forming a radial shoulder. The tongues 118 in the initial state are engaged through the central passage 104 so that the radial shoulders 124 press against the end wall 102 and thus hold the spring 112 in the loaded state.

Figures 4, 5:
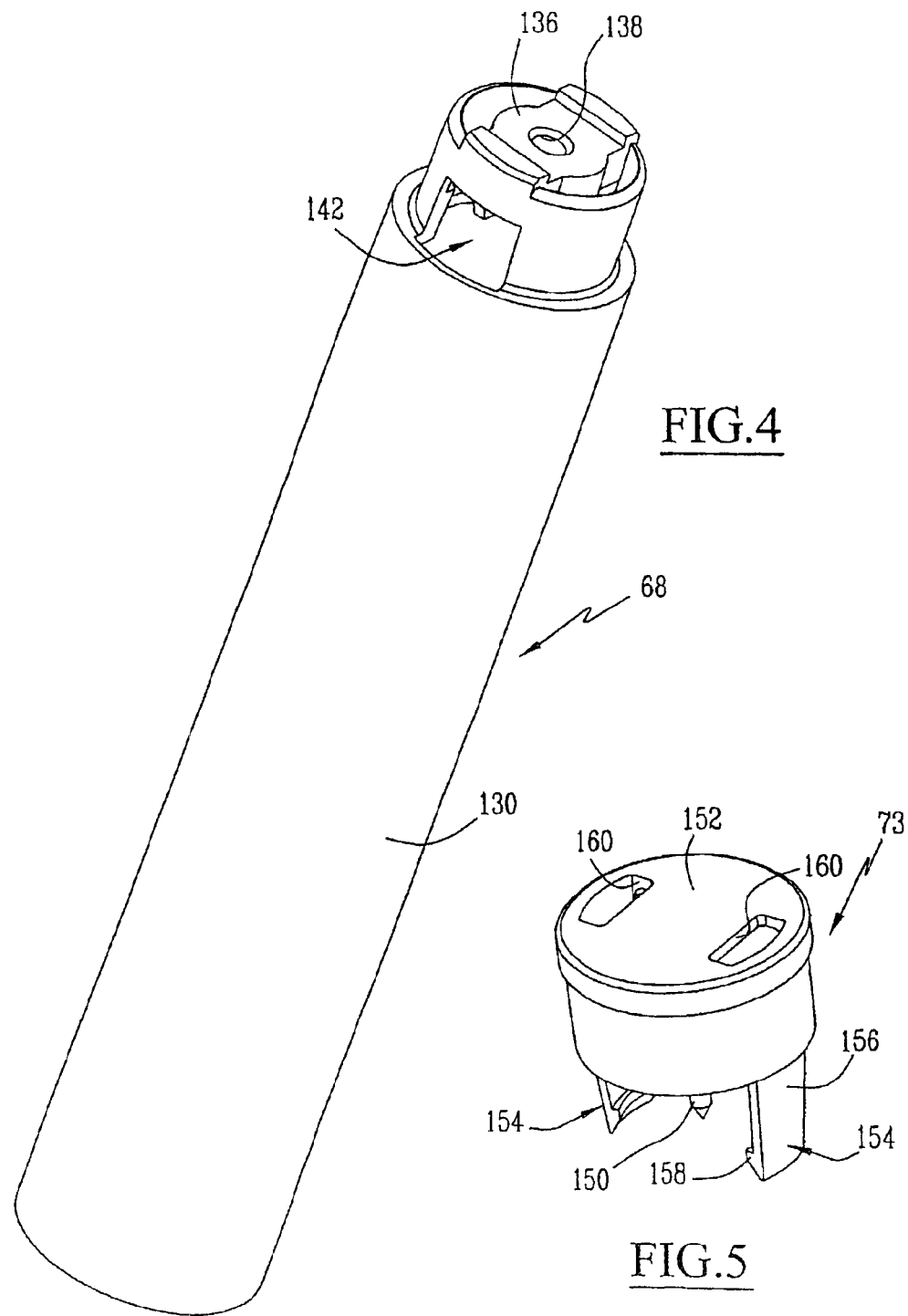
FIG. 4 is a perspective view of the syringe handle.
FIG. 5 is a perspective view of the syringe latch member.

The handle 68 shown on its own in FIG. 4 is formed essentially by a sleeve 130 completely surrounding the rear cap 64.

The handle 68 is closed in part by an axially-offset disk 136 secured to the rear end of the sleeve 130. In its initial state, the disk 136 is held at a certain distance away from the end wall 102. The disk 136 has a central duct 138 in which the chamfered ends of the lips 120 are engaged in part. As shown in FIG. 1B, the duct 138 flares progressively towards its end looking towards the lips 120.

On its inside surface, the handle 68 has longitudinal guide channels co-operating with two radial projections 140 formed on opposite sides of the end wall of the rear cap 64 so as to ensure that the handle and the rear cap are constrained to rotate together about their common axis.

On its cylindrical side surface, in the vicinity of its rear end, the handle 68 has two diametrically opposite slots 142 for passing the limbs of the means for locking the latch member 73.

The latch member 73 is shown on its own in FIG. 5, and it can be seen together with the remainder of the syringe in FIGS. 1A, 1B, 6A, and 6B.

The latch member comprises an axial safety pin 150 adapted, when the syringe is in its initial state, to be engaged through the central duct 138 so that its end extends between the tongues 118 and holds them apart from each other. The safety pin 150 is molded integrally with a cup 152 fitted onto the rear end of the handle 68.

The locking member 73 also has two diametrically opposite hooks 154 extending from the end wall of the cup 152 in directions substantially parallel to the axis of the pin 150.

Each of these hooks 154 comprises an elastically deformable limb 156 provided at its free end with a projection 158 on its inside surface.

At rest, the limbs 156 slope towards each other going towards their free ends carrying the projections 158.

To make the hooks easier to unmold, the end wall of the cup 152 presents two slots 160 that can be seen in FIG. 5.

As shown in FIG. 1, the projections 158 of the hooks are adapted, prior to the mixture being reconstituted, to be received in the slots 109 so as to prevent the latch member 73 moving axially relative to the body of the syringe, and thus lock the latch member, preventing it from being withdrawn manually before the reconstitution of the extemporaneous mixture has been completed, and in particular while the syringe is in its initial state as shown in FIG. 1A.

In order to assemble the self-injection syringe shown in FIG. 1A, the rear cap 64 is initially engaged in the handle 68. Thereafter the actuator spring 112 and the pusher 114 are inserted inside the rear cap 64 so that the lips 120 on the tongues 118 pass through the central passage 104 and the radial shoulders 124 thereof engage against the end wall of the rear cap. The latch member 74 is then put into place at the end of the rear cap 65. The pin 150 extends between the tongues 118 so as to guarantee that they are spaced apart, thereby preventing any accidental release of the spring 112.

In addition, the projections 158 formed at the ends of the hooks penetrate into the slots 109 under elastic drive from the limbs 156. The hooks are thus elastically engaged in the slots 109 at the end of the rear cap 64 and serve to hold the latch member at the end of the rear cap.

The intermediate sleeve 66 is then screwed into the rear cap 64 by engaging the complementary threads 90 and 106.

Screw tightening continues until the projections 88 are received in the first pair of housings 107 in the rear cap. In this position, the threaded segment of the rear cap 64 extends in the rear portion of the thread 90 formed along the length of the intermediate sleeve.

The safety ring 94 is then put into place between the abutment 92 and the open end of the handle 68.

With the actuator means 70 prevented from moving, the complete cartridge 12 is put into place in the intermediate sleeve 66. The front end of the cartridge is then covered by the front cap 62 fitted with the membrane 80. The cap 62 is then screwed onto the intermediate sleeve 66, thus ensuring that they are definitively connected together.

It will be understood that in this configuration, the self-injection syringe has all of its moving elements prevented from moving relative to one another and can therefore be transported and sold without presenting any risk of being triggered accidentally.

When a user seeks to self-inject the active substance contained in the injection cartridge 12, the user removes the safety ring 94.

After the safety ring 94 has been removed, the intermediate sleeve 66 can be engaged further into the rear cap 64 by screw tightening. For this purpose, the front cap 62 is turned by hand, thereby turning the sleeve 66 connected thereto.

During this screw-tightening operation, the tube 16 pressing against the front cap 62 is moved axially relative to the rear cap 64.

The partition 30 which is held pressed against the pusher 114 which is in turn prevented from moving relative to the rear cap 64 is thus progressively pushed along a rectilinear path inside the tube 16, as the tube is moved towards the rear of the syringe.

Because of the presence of the liquid 36, the intermediate piston 32 is also prevented from moving relative to the rear cap 64.

Progressive engagement of the tube 16 into the rear cap 64 leads to relative displacement between the intermediate piston 32 and the tube 16.

Thus, the piston 32 is moved into the middle segment 18 of the tube. Simultaneously, the powder 38 and the front partition 40 are moved further forwards along the tube. Once the intermediate piston is engaged in the segment 18, the channels defined by the fluting 20 are left open.

Continued screw tightening enables the fluid 36 contained in the chamber 34 to flow towards the powder 38 by flowing along the channels 22 in the fluting 20.

Progressively, as screw tightening continues, the rear partition 30 is pushed into the tube along a stroke for preparing the extemporaneous mixture. It thus expels the liquid 36 from the intermediate piston 32, which piston remains stationary in the middle segment 18 of the tube. When the liquid comes between the intermediate piston 32 and the front wall 40, it causes the front wall 40 to move towards the front of the tube.

As the liquid 36 arrives, the moving partition 40 is pushed towards the needle carrier 42. The air contained in the space 44 escapes progressively through the vents 48 provided through the needle carrier 42. For this purpose, and in order to facilitate the flow of air from the front of the tube towards the outside, the cap 62 can be provided with holes of very small diameter if the gaps between the co-operating threaded portions do not allow sufficient flow to take place.

In order to ensure that the substance 36 is transferred completely into the powder-containing chamber, the rear cap 64 is turned through about two turns.

Figure 6A:
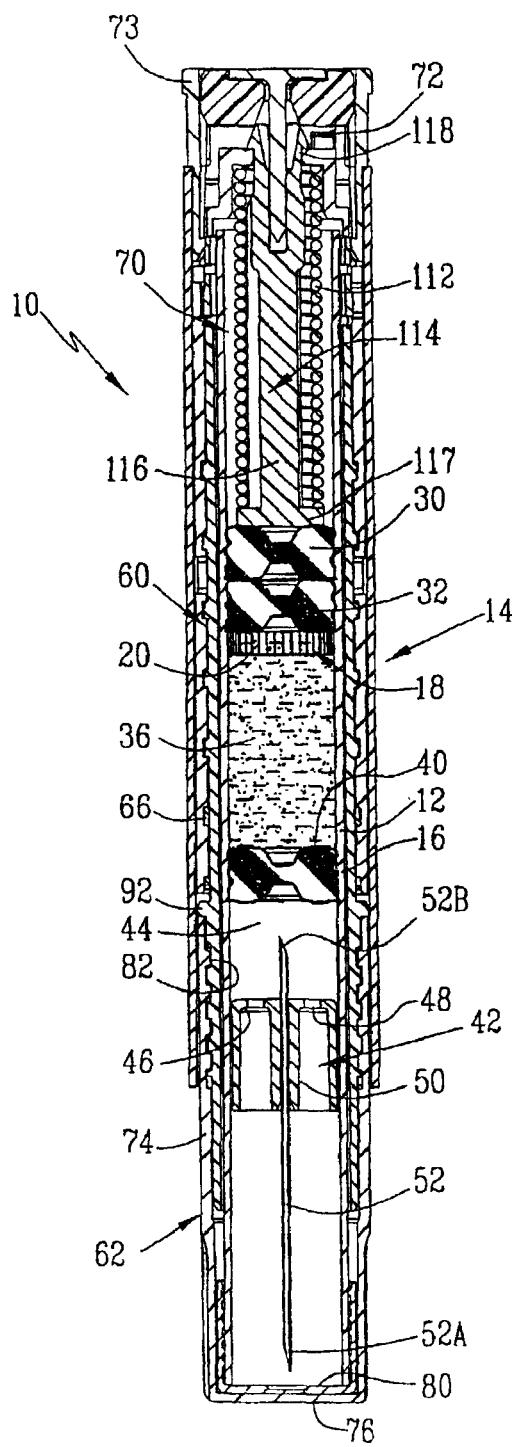
FIG. 6A is a longitudinal section view of the syringe at the end of the stage of reconstituting the extemporaneous mixture.
Figure 6B:
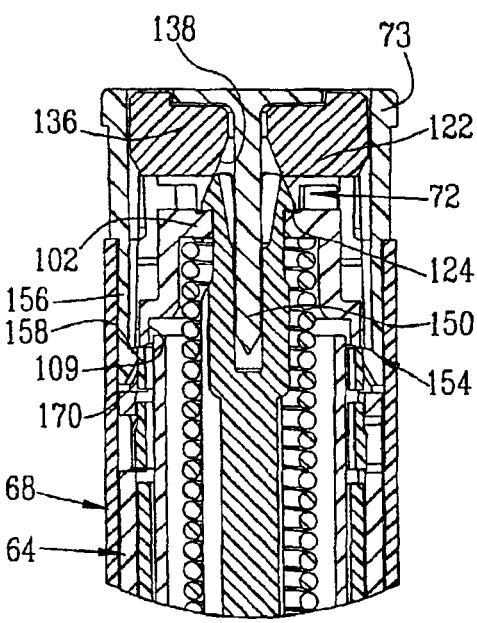
FIG. 6B is a longitudinal section view on a larger scale showing the rear end of the syringe in its FIG. 6A state.

At the end of this screw tightening, as shown in FIGS. 6A and 6B, the rear partition 30 reaches the end of its stroke for preparing the extemporaneous mixture. It is then in contact with the intermediate piston 32 while the front partition 40 extends immediately behind the tip 52B of the needle. In this position, nearly all of the liquid 36 that was initially contained in the chamber 34 has been transferred to between the intermediate piston 32 and the front partition 40.

In the final stage of engaging the intermediate sleeve 66 further into the rear cap 64, the rear end of the sleeve comes into contact with the projections 158 of the hooks engaged in the slots 109. Under drive from the displacement of the intermediate sleeve, the projections are progressively pushed outwards until they have been removed completely from the slots 109.

Once this screw tightening has terminated, the rear end of the intermediate sleeve 66 bears against the rear cap, and in particular against the thickness of the cylindrical segment 101. In this position, areas referenced 170 forming disengagement surfaces defined on the outside surface of the intermediate sleeve 66 between its rear end and the edge of the slot 86 extend in the slots 109 in the locations initially occupied by the projections 158 of the hooks.

The presence of these surfaces 170 in the slots 109 ensures that the projections 158 are held away from the extension of the side surface of the rear cap 64, thus releasing elastic engagement of the hooks 154 in the slots 109.

It will be understood that in this position the latch member 73 can be withdrawn manually by pulling on it and extracting it along the axis of the syringe.

While the latch member is being withdrawn, the safety pin is withdrawn into the space between the tongues 118, thereby releasing them.

In order to process with injection proper, the front end of the syringe as shown in FIGS. 7A and 7B is pressed against the region of the body that is to be injected. The operator then pushes the handle 68 forwards. This causes the disk 136 to act on the resilient tongues 118 and leads to the lips 120 being moved towards each other. Once they are close enough together, the pusher 114 is released from the passage 104 under the effect of the compressed actuator spring 122. This spring then pushes back the pusher 114. The pusher acts on the elements contained in the tube 16 and causes them to move towards the needle 52. In particular, when the front partition 40 reaches the tip 52B of the needle, it becomes impaled thereon, thus causing the needle to come into contact with the reconstituted active substance comprising the mixture of the powder 38 and the liquid 36. The needle carrier 42 is then projected towards the front end of the tube 16. The needle 52 then passes through the membrane 80 and then the closing end wall 76, and finally penetrates into the user's tissue.

Figure 8:
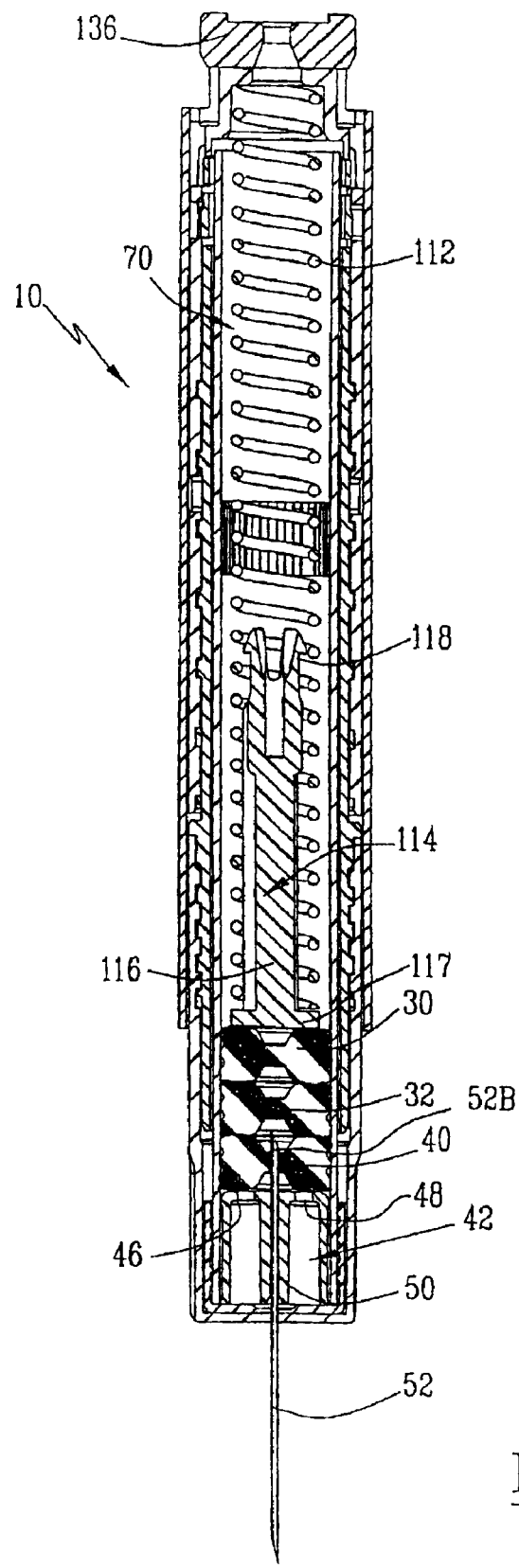
FIG. 8 is a longitudinal section view of the syringe after injection.

Continued relaxation of the actuator spring 112 causes the active substance contained between the intermediate piston 32 and the front partition 40 to be injected into the user's tissue through the injection needle 52. At the end of injection, the syringe is in the position shown in FIG. 8. The injection step proper takes place very quickly once the spring has been released, thus eliminating any feeling of pain by the user.

It will be understood that with a syringe as described above, since the latch member 73 is fitted with locking means that prevent it from being withdrawn until the extemporaneous mixture has been fully reconstituted, the means for automatically injecting the extemporaneous mixture cannot be triggered until such reconstitution has been completed, since the latch member prevents such triggering and said latch member cannot itself be withdrawn until reconstitution has been completed.

Thus, if the operator seeks to proceed with the injection before reconstitution has been completed, the operator cannot withdraw the latch member and therefore cannot trigger the automatic injection means, and as a result does not run the risk of injecting a substance that has not been reconstituted. Since the user cannot withdraw the latch member, it will be clear to the user that reconstitution of the extemporaneous mixture has not been completed so the user will continue turning the two complementary portions of the body until reconstitution has been completed, and only then can the latch member be withdrawn and automatic injection of the extemporaneous mixture triggered.

What is claimed is:

1. A syringe for self-injecting an extemporaneous mixture, the syringe being of the type comprising:

a body containing at least two substances initially separated by an intermediate piston, which body has two relatively movable portions that are movable between an initial position in which the two substances are separate and a final position in which the two substances are mixed together to form an extemporaneous mixture;

automatic injection means for injecting the extemporaneous mixture out from the body in order to proceed with injection; and latch means for preventing triggering of the automatic injection means;

wherein the syringe comprises locking means for locking the latch means that prevents the automatic injection means from being triggered before the two substances have finished being mixed together, wherein the latch means comprises a latch member movable between an active position, for latching the automatic injection means, and an inactive position where the automatic injection means are not latched, the locking means including complementary hooking profiles for hooking by elastic engagement provided on said latch member and on a first moving portion of the body, said complementary hooking profiles being normally mutually engaged, and wherein the second moving portion of the body includes at least one surface for disengaging the complementary hooking profiles and adapted to disengage said complementary hooking profiles only when the two moving portions of the body are in their final position.

2. A self-injection syringe according to claim 1, wherein said complementary hooking profiles comprise firstly at least one hook secured to said latch member, and secondly at least one slot formed in said first moving portion, the or each hook being urged elastically to be received at least in part in an associated slot, and wherein the or each engagement surface is adapted to extend in the or each slot to push the or each associated hook filly out from the slot only once the two moving portions are in their final position.

3. A self-injection syringe according to claim 1, wherein said latch member is removable.

4. A self-injection syringe according to claim 2, wherein said latch member is removable.

* * * * *